US006521433B1

(12) United States Patent
Fader

(10) Patent No.: US 6,521,433 B1
(45) Date of Patent: Feb. 18, 2003

(54) CDNA SEQUENCES FROM PLANTS THAT ENCODE ACTIVITIES ASSOCIATED WITH ISOFLAVONE BIOSYNTHESIS

(75) Inventor: Gary Michael Fader, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 08/931,668

(22) Filed: Sep. 17, 1997

(51) Int. Cl.[7] .............................. C12N 9/02; C12N 1/21; C12N 5/04; C07H 21/04
(52) U.S. Cl. .................... 435/189; 435/252.5; 435/410; 435/254.11; 435/254.2; 435/320.1; 536/23.2
(58) Field of Search .......................... 435/252.3, 320.1, 435/410, 6, 189, 254.11, 254.2, 254.4; 536/23.2, 23.6, 24.3, 24.33, 22.2

(56) References Cited

U.S. PATENT DOCUMENTS

| | | | | |
|---|---|---|---|---|
| 4,945,050 | A | 7/1990 | Sanford et al. ............. | 435/459 |
| 5,107,065 | A | 4/1992 | Shewmaker et al. ........ | 800/298 |
| 5,231,020 | A | 7/1993 | Jorgensen et al. .......... | 800/281 |
| 5,561,236 | A | 10/1996 | Leemans et al. ............ | 800/300 |
| 5,646,024 | A | 7/1997 | Leemans et al. ............... | 435/6 |
| 5,750,399 | A * | 5/1998 | Dixon et al. ................ | 435/419 |

FOREIGN PATENT DOCUMENTS

WO    WO 96/15239    5/1996

OTHER PUBLICATIONS

Chu et al., *Sci. Sin. Peking*, 18, 659–668, 1975.
Deblaere et al., *Meth. Enzymol.*, 153, 277–292, 1987.
Hoheisel, J.D. et al., In Nonmammalian Genomic Analysis: A Practical Guide, *Academic Press*, 319–346, 1996.
Altschul, S. F. et al., *J. Mol. Biol.*, 215, 403–410, 1990.
Jones et al., *EMBO J.*, 4, 2411–2418, 1985.
Keegstra, K., *Cell*, 56, 247–253, 1989.
*Biochemical Journal*, 219(2), 345–373, 1984.
Kitamura et al., *J. Breed*, 41, 651–654, 1991.
Mathur et al., *J. Nutrition*, 84, 201–204, 1964.
Adams, M.D. et al., *Science*, 252, 1651, 1991.
Laan et al., *Genome Research*, 5, 13–20, 1995.
Lander et al., *Genomics*, 1, 174–181, 1987.
Botstein, D. et al., *Am. J. Hum. Genet.*, 32, 314–331, 1980.
Bernatzky, R. and Tanksley, S.D., *Plant Mol. Biol. Reporter*, 4(1), 37–41, 1986.
*Nucleic Acids Research*, 13, 3021–3030, 1985.
Odell et al., *Nature*, 313, 810–812, 1985.
De Almeida et al., *Mol. Gen. Genetics*, 218, 78–86, 1989.
Loh et al., *Science*, 243, 217, 1989.
Dixon, R. A. and Paiva, N. L., *The Plant Cell*, 7, 1085–1097, 1995.
R. D. Sharma, *Lipids*, 14(6), 535–540, 1978.
Studier et al., *J. Mol. Biol.*, 189, 113–130, 1986.

Kazazian et al., *J. Lab. Clin. Med.*, 114, 95–96, 1989.
Okamuro and Goldberg, *Biochemistry of Plants*, 15, 1–82, 1989.
Ingelbrecht et al., *Plant Cell*, 1, 671–680, 1989.
Gish, W. and States, D. J., *Nature Genetics*, 3, 266–272, 1993.
Klein et al., *Nature (London)*, 327, 70–73, 1987.
Ohara et al., *PNAS USA*, 86, 5673, 1989.
Frohman, M. A. and Martin, G. R., *Techniques*, 1, 165, 1989.
Rosenberg et al., *Gene*, 56, 125–135, 1987.
Tsukamoto et al., *J. Agric. Food Chem.*, 43, 1184–1192, 1995.
Messina, M. and Barnes, S., *Commentary*, 83(8), 541–546, 1991.
Dear and Cook, *Nucleic Acids Research*, 17, 6795–6807, 1989.
Walter et al., *Nature Genetics*, 7, 22–28, 1987.
Raikhel, *Plant Phys.*, 100, 1627–1632, 1992.
Turner, R. and Foster, G.D., *Molecular Biotechnology*, 3, 225, 1995.
Fromm et al., *Bio/Technology*, 8, 833–839, 1990.
Trask et al., *Trends Genet.*, 7, 149–154, 1991.
Ballinger et al., *Proc. Natl. Acad. Sci.*, 86, 9402–9406, 1989.
Landengren et al., *Science*, 241, 1077–1080, 1988.
Koes et al., *Proc. Natl. Acad. Sci.*, 92, 8149, 1995.
Peterson, G. and Barnes, S., *Biochem. and Biophsy. Res. Com.*, 179(1), 661–667, 1991.
Naim et al., *J. Agr. Food Chem.*, 22(5), 806–810, 1974.
Sokolov B. P., *Nucl. Acids Res.*, 18(12), 3671, 1989.
Bensen et al., *The Plant Cell*, 7, 75–84, 1995.
Lerner, R.A., *Adv. Immunol.*, 36, 1 Maniatis, 1984.
Frohman et al., *PNAS USA*, 85, 8998, 1988.
Chrispeels, J.J., *Ann. Rev. Plant Phys. Plant Mol. Biol.*, 42, 21–53, 1991.
Doyle et al., *J. Biol. Chem.*, 261, 9228–9238, 1986.
Gritz, L. et al., *Gene*, 25, 179–188, 1985.
Sheffield et al., *Genomics*, 16, 325–332, 1993.
Price, K. R and Fenwick, G. R., *Food Additives and Contaminates*, 2, 73–106, 1985.
Naim et al., *J. Agric. Food Chem.*, 24(6), 1174–1177, 1976.
Wang et al., *J. Agric. Food Chem.*, 42, 1674–1677, 1994.
Terai et al., Protein Expr. Purif., vol. 8(2), 1996 pp. 183–190.
Swiss–Prot: Locus IFRI Lupal, Accession P52581.

(List continued on next page.)

*Primary Examiner*—Elizabeth Slobodyansky

(57) ABSTRACT

This invention relates to an isolated nucleic acid fragment encoding soybean enzymes that catalyze steps in biosynthesis of isoflavones, the enzyme a member selected from the group consisting of chalcone isomerase, isoflavone reductase and vestitone reductase. The invention also relates to the construction of chimeric genes encoding all or a substantial portion of the enzymes, in sense or antisense orientation, wherein expression of the chimeric gene results in production of altered levels of the enzyme in a transformed host cell.

11 Claims, 4 Drawing Sheets

OTHER PUBLICATIONS

Genbank: Locus MSU28213, Accession U28213.

Atfucci et al. Genbank: Locus LAU48590, Accession U48590.

DDBJ: Locus Puechi, Accession D63577.

Teral, Y., et al., Cloning and Overexpression of the Chalcone–Flavanone Isomerase cDNA from *Pueraria lobata*, *EMBL Sequence Data Library*, Aug. 15, 1995, XP002090217.

Scolnik, P.A. and Barley, G.E., Two Members of an *Arabidopsis Geranylgeranyl* Pyrophosphate Synthase Gene Family, *EMBL Sequence Data Library*, Mar. 23, 1996, XP002090218.

Guo, L. and Paiva, N.L., Molecular Cloning and Expression of Alfalfa (*Medicago sativa* L.) Vistitone Reductase, the Penultimate Enzyme in Medicarpin Biosynthesis, *Archives of Biochemistry and Biophysics*, 320, No. 2, 353–360, Jul. 1995.

Paiva N.L., Biotransformation of Isoflavonoids by Transgenic Tobacco Cell Cultures, *Abstracts of Papers, ACS National Meeting*, 1/02, 129, Apr. 2, 1995.

Paiva, N.L. et al., Stress Responses in Alfalfa (*Medicago sativa* L.) 11 molecular Cloning and Expression of Alfalfa Isoflavone Reductase, A Key Enzyme of Isoflavonoid Phytoalexin Biosynthesis Plant Molecular Biology, *Plant Molecular Biology*, 17, 653–667, Oct. 1, 1991.

Seehaus, K. and Tenhaken, R., Cloning of Genes by mRNA Differential Display Associated with the Hypersensitive Reaction of Soybean After Inoculation with *Pseudomdonas Syringae* pv. Glycinea, *EMBL Sequence Data Library*, Aug. 25, 1998, XP002090220.

Schopfer, C.R., Unpublished, *EMBL Sequence Data Library*, Dec. 11, 1997, XP002090221.

Newman et al. (1994) Genes Galore: A Summary of Methods for Accessing Results from Large–Scale Partial Sequencing of Anonymous Arabidopsis cDNA Clones. Plant Physiology, vol. 106, pp. 1241–1255.*

Dinkova–Kostova et al. (Nov. 15, 1996) (+)–Pinoresinol/(+)–Lariciresinol Reductase from *Forsythia intermedia*. J. Biol. Chem., vol. 271, pp. 29473–29482.*

* cited by examiner

FIG. 2

```
        10            20            30            40
  1   M A A A A A V A T I S A V Q V E F L E F P A V V T S P A S G R T Y F L G G A G E   D63577
  1   M - - - - - A T I S A V Q V E F L E F P A V V T S P A S G K T Y F L G G A G E   ssm.pk0013.e3

50            60            70            80
 41   R G L T I E G K F I K F T G I G V Y L E D K A V S S L A A K W K G K P S E E L V   D63577
 35   R G L T I E G K F I K F T G I G V Y L E D K A V P S L A A K W K G K T S E E L V   ssm.pk0013.e3

90           100           110           120
 81   E T L D F Y R D I I S G P F E K L I R G S K I L P L S G V E Y S K K V M E N C V   D63577
 75   H T L H F Y R D I I S G P F E K L I R G S K I L P L A G A E Y S K K K V M E N C V   ssm.pk0013.e3

130           140           150           160
121   A H M K S V G T Y G D A E A A A I E K F A E A F K N V N F Q P G A T V F Y R Q S   D63577
115   A H M K S V G T Y G D A E A A A A I E K F A E A F K N V N F A P G A S V F Y R Q S   ssm.pk0013.e3

170           180           190           200
161   P D G V L G L S F S E D V T I P D N E A A V I E N K A V S A A V L E T M I G E H   D63577
155   P D G I L G L S F S E D A T I P E K E A A V I E N K A V S A A V L E T M I G E H   ssm.pk0013.e3

210           220
201   A V S P D L K R S L A S R L P A V L S H G I I V .   D63577
195   A V S P D L K R S L A S R L P A V L S H G I I V .   ssm.pk0013.e3
```

```
            10              20              30              40              50
  1  M A E G K G R V C V T G G T G F L G S W I I K S L L E N G Y S V N T T T I R A D P E R K R D V S F L T   U28213
  1  M G E G K G R I C V T G G T G F L G S W I I K S L L E H G Y A V N T T I R S D P G R K R D V S F L T   sre.pk0016.c8

60              70              80              90             100
 51  N L P G A S E K L H F F N A D L S N P D S F A A A I E G C V G I F H T A S P I D F A V S E P E E I V   U28213
 51  N L P G A S E K L K I F N A D L S D P E S F G P A V E G C V G I F H T A T P I D F A V N E P E E V V   sre.pk0016.c8

110             120             130             140             150
101  T K R T V D G A L G I L K A C V N S K T V K R F I Y T S S G S A V S F N G - K D K D V L D E S D W S   U28213
101  T K R R A I D G A L G I L K A G L K A K T V K R V V V Y T S S A S T V S F S S L E E K D V V D E S V W S   sre.pk0016.c8

160             170             180             190             200
150  D V D L L R S V K P F G W N Y A V S K T L A E K A V L E F G E Q N G I D V V T L I L P F I V G R F V   U28213
151  D V D L L R S V K P F S W S Y A V S K V L S E K A V L E F G E Q N G L E V T T L V L P F V V G R F V   sre.pk0016.c8

210             220             230             240             250
200  C P K L P D S I E K A L V L V L G K K E Q I G V T R F H M V H V D D V A R A H I Y L L E N S V P G G   U28213
201  C P K L P D S V E R A L L L V L G K K E E I G V I R Y H M V H V D D V A R A H I F L L E H P N P K G   sre.pk0016.c8

260             270             280             290             300
250  R Y N C S P F I V P I E E M S Q L L S A K Y P E Y Q I L T V D E L K E I K G A R L P D L N T K K L V   U28213
251  R Y N C S P F I V P I E E I A E I I S A K Y P E Y Q I P A L E E V K E I K G A K L P H L T S Q K L V   sre.pk0016.c8

310             320
300  D A G F D F K Y T I E D M F D D A I Q C C K E K G Y - L .                                             U28213
301  D A G F E F K Y S V E D I F T D A I E C C K E K G Y L .                                               sre.pk0016.c8
```

CDNA SEQUENCES FROM PLANTS THAT ENCODE ACTIVITIES ASSOCIATED WITH ISOFLAVONE BIOSYNTHESIS

FIELD OF THE INVENTION

This invention is in the field of plant molecular biology. More specifically, this invention pertains to nucleic acid fragments encoding enzymes involved in isoflavone biosynthesis in plants and seeds.

BACKGROUND OF THE INVENTION

Isoflavones represent a class of secondary metabolites produced in legumes by the phenylpropanoid metabolic pathway. The biosynthetic pathway for free isoflavones and their relationship with several other classes of phenylpropanoids is presented in FIG. 1. Many of the enzymes involved in the synthesis of isoflavones in soybean have been identified and the genes in the pathway from phenylalanine ammonia lyase to chalcone synthase and chalcone reductase have been cloned. However, remaining soybean genes involved in synthesis (chalcone isomerase and isoflavone synthase), further metabolism (isoflavone reductase and vestitone reductase), and branch points of the isoflavone pathway that could compete for substrates (flavanone hydroxylase and flavonol synthase) heretofore have not been available.

Free isoflavones rarely accumulate to high levels in soybeans. Instead they are usually conjugated to carbohydrates or organic acids. Soybean seeds contain three types of isoflavones in four different forms: the aglycones daidzein, genistein, and glycitein; the glucosides diadzin, genistin, and glycitin; the acetylgucosides 6"-O-acetyldaidzin, 6"-O-acetylgenistin, and 6"-O-acetylglycitin; and the malonylglucosides 6"-O-malonyldaidzin, 6"-O-malonylgenistin, and 6"-O-malonylglycitin. It has been reported that the isoflavones found in soybean seeds possess antihemolytic (Naim, M. et al. (1976) *J. Agric. Food Chem.* 24:1174–1177), antifungal (Naim, M. et al. (1974) *J Agr. Food Chem.* 22:806–810), oestrogenic (Price, K. R. and Fenwick, G. R. (1985) *Food Addit. Contam.* 2:73–106), tumor suppressing (Messina, M. and Barnes, S. (1991) *J. Natl. Cancer Inst.* 83:541–546; Peterson, G. et al. (1991) *Biochem. Biophys. Res. Commun.* 179:661–667), hypolipidemic (Mathur, K. et al. (1964) *J. Nutr.* 84:201–204), and serum cholesterol lowering (Sharma, R. D. (1979) *Lipids* 14:535–540) effects. These epidemiological studies indicate that when isoflavone levels are high in soybean seeds and in the subsequent commercial protein products made from the seeds, the dietary intake of these products provide many health benefits.

The content of isoflavones in soybean seeds, however, is quite variable and is affected by both genetics and environmental conditions such as growing location and temperature during seed fill (Tsukamoto, C. et al. (1995) *J. Agric. Food Chem.* 43:1184–1192; Wang, H. and Murphy, P. A. (1994) *J. Agric. Food Chem.* 42:1674–1677). In addition, isoflavone content in legumes can be stress-induced by pathogenic attack, wounding, high UV light exposure, and pollution (Dixon, R. A. and Paiva, N. L. (1995) *The Plant Cell* 7:1085–1097). To date, it has proven difficult to develop soybean lines with consistantly high levels of isoflavones; moreover, lines reported to be low in isoflavone content produced normal levels of isoflavones when grown under standard cultural conditions (Kitamura, K. et al. (1991) *Jap. J. Breed.* 41:651–654). The isolation and cloning of genes associated with synthesis and metabolism of isoflavones in soybean will afford the application of molecular techniques to achieve stable, high level accumulation of isoflavones.

SUMMARY OF THE INVENTION

The instant invention relates to isolated nucleic acid fragments encoding plant enzymes involved in isoflavone biosynthesis. Specifically, this invention concerns isolated nucleic acid fragments encoding the following soybean enzymes that catalyze steps in the biosynthesis of isoflavones from phenylalanine: chalcone isomerase, isoflavone reductase and vestitone reductase. In addition, this invention relates to nucleic acid fragments that are complementary to nucleic acid fragments encoding the listed soybean biosynthetic enzymes.

In another embodiment, the instant invention relates to chimeric genes encoding the isoflavone biosynthetic acid enzymes listed above or to chimeric genes that comprise nucleic acid fragments that are complementary to the nucleic acid fragments encoding the enzymes, operably linked to suitable regulatory sequences, wherein expression of the chimeric genes results in production of levels of isoflavone biosynthetic enzymes in transformed host cells that are altered (i.e., increased or decreased) from the levels produced in untransformed host cells.

In a further embodiment, the instant invention concerns a transformed host cell comprising in its genome a chimeric gene encoding an isoflavone biosynthetic enzyme operably linked to suitable regulatory sequences, the enzyme selected from the group consisting of chalcone isomerase, isoflavone reductase and vestitone reductase. Expression of the chimeric gene results in production of altered levels of the biosynthetic enzyme in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a plant isoflavone biosynthetic enzyme in a transformed host cell comprising: a) transforming a host cell with a chimeric gene comprising a nucleic acid fragment encoding a soybean isoflavone biosynthetic enzyme selected from the group consisting of chalcone isomerase, isoflavone reductase and vestitone reductase, operably linked to suitable regulatory sequences; and b) growing the transformed host cell under conditions that are suitable for expression of the chimeric gene wherein expression of the chimeric gene results in production of altered levels of an isoflavone biosynthetic enzyme in the transformed host cell.

An additional embodiment of the instant invention concerns a method for obtaining a nucleic acid fragment encoding all or substantially all of an amino acid sequence encoding a plant chalcone isomerase, isoflavone reductase and vestitone reductase.

BRIEF DESCRIPTION OF THE DRAWINGS AND SEQUENCE DESCRIPTIONS

The invention can be more fully understood from the following detailed description and the accompanying drawings and sequence descriptions which form a part of this application.

FIG. 2 shows a comparison of the amino acid sequences of the *Pueraria lobata* chalcone flavanone isomerase (D63577) and the instant soybean chalcone isomerase (ssm.pk0013.e3).

Figure 3:
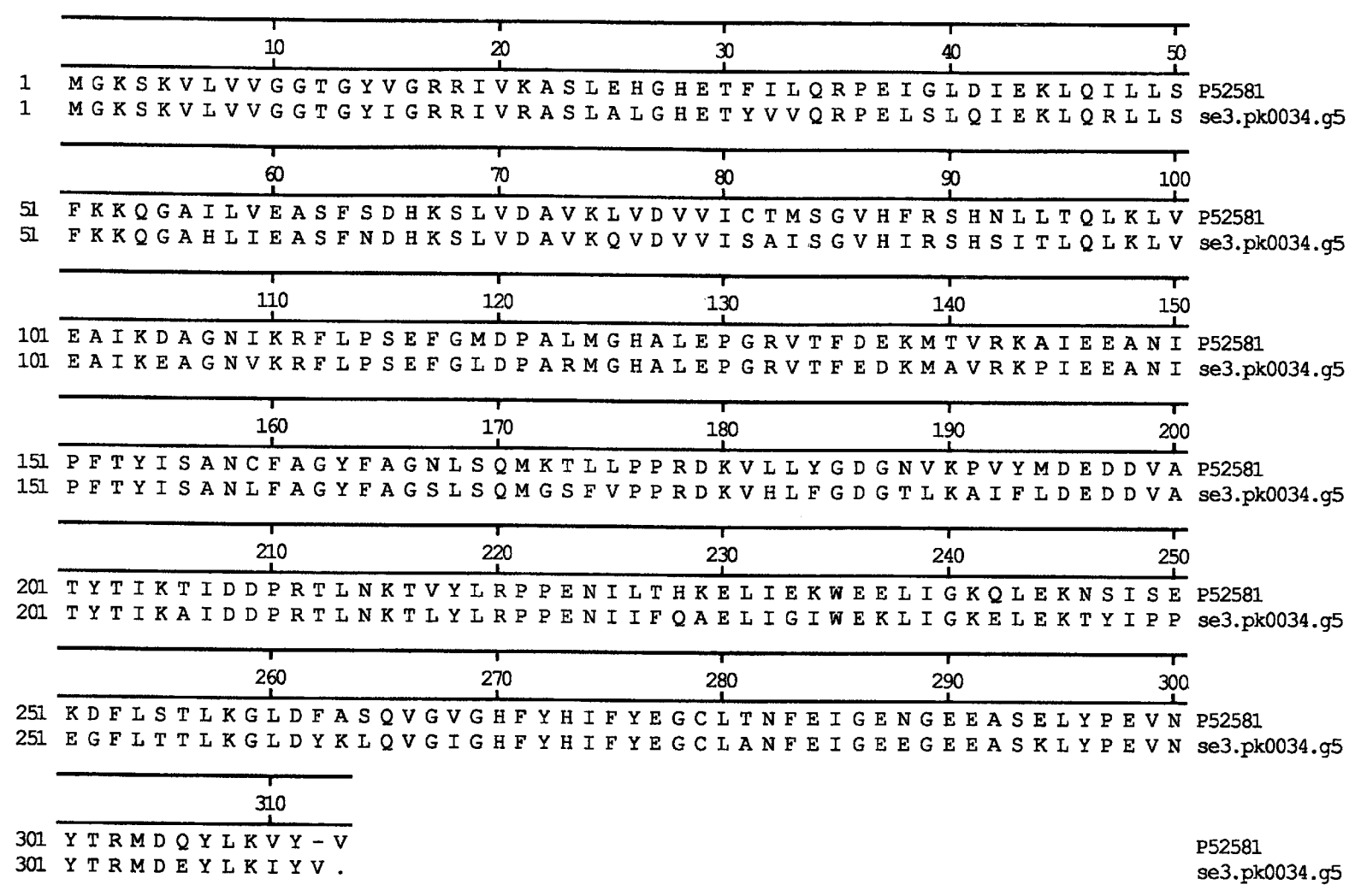

FIG. 3 shows a comparison of the amino acid sequences of the isoflavone reductase homolog from *Lupinus albus* (P52581) and the instant soybean isoflavone reductase (se3.pk0034.g5).

FIG. 4 shows a comparison of the amino acid sequences of the *Medicago sativa* vestitone reductase (U28213) and the instant soybean vestitone reductase (sre.pk0016.c8).

Figure 1:
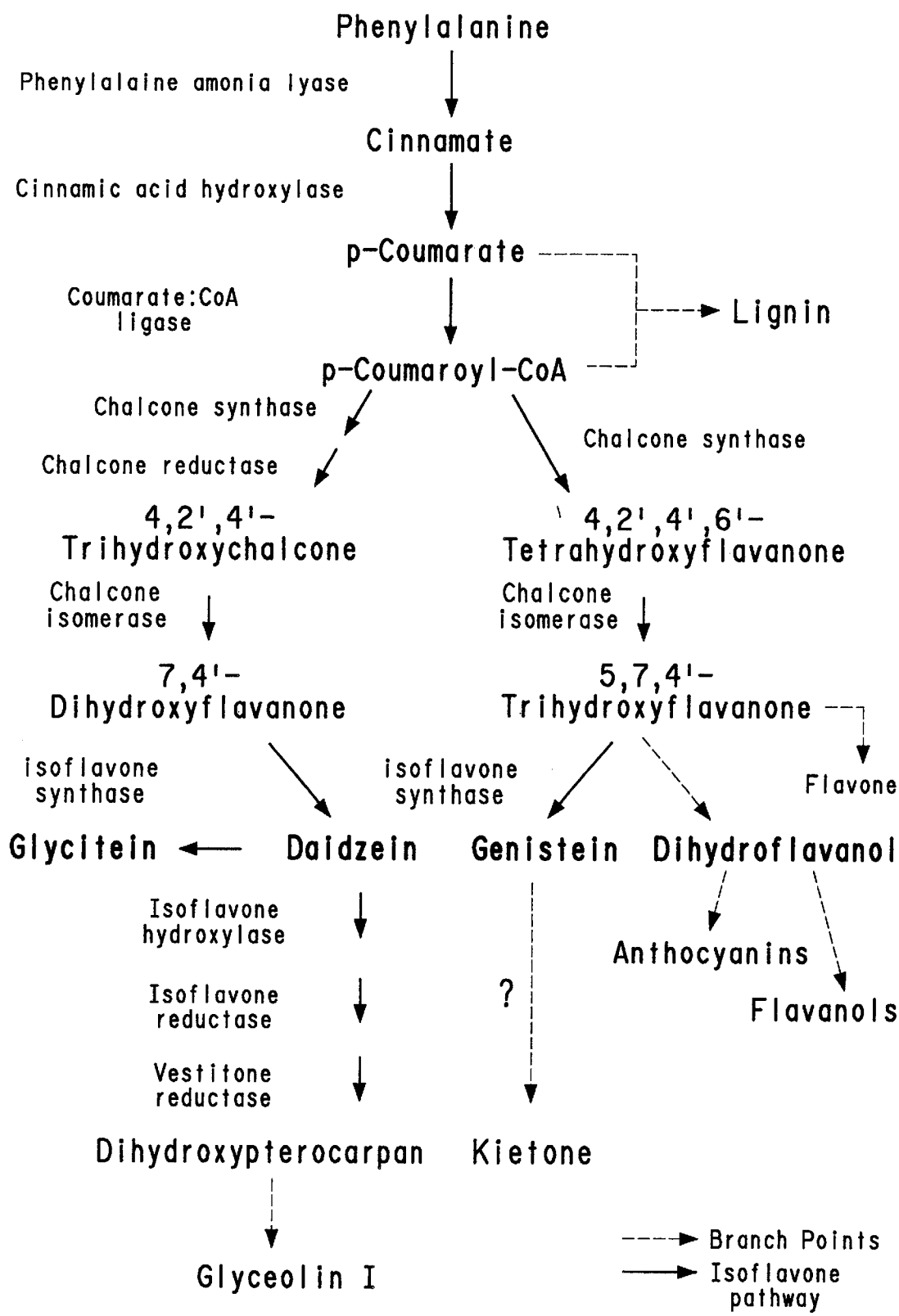
FIG. 1 depicts the phenylpropanoid metabolic pathway illustrating the biosynthesis of isoflavones.

The following sequence descriptions and sequences listings attached hereto comply with the rules governing nucleotide and/or amino acid sequence disclosures in patent applications as set forth in 37 C.F.R. §1.821–1.825.

SEQ ID NO:1 is the nucleotide sequence comprising part of the cDNA insert in clone ssm.pk0013.e3 encoding a soybean chalcone isomerase.

SEQ ID NO:2 is the deduced amino acid sequence of a soybean chalcone isomerase derived from the nucleotide sequence of SEQ ID NO:1.

SEQ ID NO:3 is the amino acid sequence encoding the *Pueraria lobata* chalcone flavanone isomerase having DDJB Accession No. D63577.

SEQ ID NO:4 is the nucleotide sequence comprising part of the cDNA insert in clone se3.pk0034.g5 encoding a soybean isoflavone reductase.

SEQ ID NO:5 is the deduced amino acid sequence of a soybean isoflavone reductase derived from the nucleotide sequence of SEQ ID NO:4.

SEQ ID NO:6 is the amino acid sequence encoding the isoflavone reductase homolog from *Lupinus albus* having SWISS-PROT Accession No. P52581.

SEQ ID NO:7 is the nucleotide sequence comprising part of the cDNA insert in clone sre.pk0016.c8 encoding a soybean vestitone reductase.

SEQ ID NO:8 is the deduced amino acid sequence of a soybean vestitone reductase derived from the nucleotide sequence of SEQ ID NO:7.

SEQ ID NO:9 is the amino acid sequence encoding the *Medicago sativa* vestitone reductase having GenBank Accession No. U28213.

The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

The instant invention discloses the amino acid sequence for three enzymes involved in the synthesis and metabolism of isoflavones in soybeans: chalcone isomerase, isoflavone reductase and vestitone reductase. As these genes code for enzymes nearer to the desired isoflavones in the phenylpropanoid pathway (see FIG. 1), they may be more useful in manipulating isoflavone content without affecting other portions of the phenylpropanoid pathway associated with lignin, anthocyanin or flavonol biosynthesis.

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less that the entire coding region of a gene, and by nucleic acid fragments that do not share 100% identity with the gene to be suppressed. Moreover, alterations in a gene which result in the production of a chemically equivalent amino acid at a given site, but do not affect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1X SSC, 0.1% SDS, 65° C.), with the sequences exemplified herein. Preferred substantially similar nucleic acid fragments of the instant invention are those nucleic acid fragments whose DNA sequences are 80% identical to the DNA sequence of the nucleic acid fragments reported herein. More preferred nucleic acid fragments are 90% identical to the identical to the DNA sequence of the nucleic acid fragments reported herein. Most preferred are nucleic acid fragments that are 95% identical to the DNA sequence of the nucleic acid fragments reported herein.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) J. Mol. Biol. 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment that encodes all or a substantial portion of the amino acid sequence encoding the isoflavone biosynthetic enzymes as set forth in SEQ ID NOS:2, 5 and 8. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of anti sense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 153:277) and particle-accelerated or "gene gun" transformation technology (Klein et al. (1987) *Nature* (*London*) 327:70–73; U.S. Pat. No. 4,945,050).

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, 1989 (hereinafter "Maniatis").

Nucleic acid fragments encoding several soybean isoflavone biosynthetic enzymes have been isolated and identified by comparison of random plant cDNA sequences to public databases containing nucleotide and protein sequences using the BLAST algorithms well known to those skilled in the art. Table 1 lists the isoflavone biosynthetic enzymes that are described herein, and the designation of the cDNA clones that comprise the nucleic acid fragments encoding these enzymes.

TABLE 1

| Isoflavone Biosynthetic Enzymes | |
|---|---|
| Enzyme | Clone |
| chalcone isomerase | ssm.pk0013.e3 |
| isoflavone reductase | se3.pk0034.g5 |
| vestitone reductase | sre.pk0016.c8 |

The nucleic acid fragments of the instant invention may be used to isolate cDNAs and genes encoding homologous enzymes from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other isoflavone biosynthetic enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *BioTechniques* 1:165).

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which expression of nucleic acid sequences (or their complements) encoding the disclosed biosynthetic enzymes result in levels of the corresponding endogenous enzymes that are higher or lower than normal. Alternatively, expression of the instant nucleic acid sequences may result in the production of the encoded enzymes in cell types or developmental stages in which they are not normally found. Either strategy would have the effect of altering the level of isoflavones.

For example, overexpression of chalcone isomerase may result in an increase in isoflavone content in legumes, and anthocyanin, flavone and flavanols in other plant species. Chalcone isomerase overexpression may result in an increase in levels of 7,4'-dihydroxyflavone and 5,7,4'-trihydroxyflavone, precursors in the biosynthetic pathways leading to isoflavone, flavone and dihydroflavanol (which upon continuation leads to anthocyanin and flavanols) synthesis (see FIG. 1). Increased isoflavone content in legumes has been shown to be associated with beneficial health effects in humans. In contrast, certain soy food products would benefit from lower levels of isoflavone, flavone, anthocyanins and flavanols due to adverse effects on flavor. Accordingly, in some applications, decreased chalcone isomerase activity, induced by antisense suppression or co-suppression of gene expression, may be desireable.

Likewise, overexpression of isoflavone reductase and vestitone reductase could lead to increased metabolism of isoflavones in legumes, resulting in lower levels of isoflavones. Conversly, inhibition of expression of genes encoding isoflavone reductase and vestitone reductase may result in increased isoflavone content by reducing isoflavone metabolism by these enzymes.

Overexpression of the biosynthetic enzymes of the instant invention may be accomplished by first constructing chimeric genes in which the coding regions are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals may also be provided. The instant chimeric genes may also comprise one or more introns in order to facilitate gene expression.

Plasmid vectors comprising the instant chimeric genes can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant biosynthetic enzymes to different cellular compartments, or to facilitate their secretion from the cell. It is thus envisioned that the chimeric genes described above may be further supplemented by altering the coding sequences to encode enzymes with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of the genes encoding isoflavone biosynthetic enzymes in plants for some applications. In order to accomplish this, chimeric genes designed for co-suppression of the instant biosynthetic enzymes can be constructed by linking the genes or gene fragments encoding the enzymes to plant promoter sequences. Alternatively, chimeric genes designed to express antisense RNA for all or part of the instant nucleic acid fragments can be constructed by linking the genes or gene fragment in reverse orientation to plant promoter sequences. Either the co-suppression or antisense chimeric genes could be introduced into plants via transformation wherein expression of the corresponding endogenous genes are reduced or eliminated.

The instant isoflavone biosynthetic enzymes (or portions of the enzymes) may be produced in heterologous host cells, particularly in the cells of microbial hosts, and can be used to prepare antibodies to the enzymes by methods well known to those skilled in the art. The antibodies are useful for detecting the enzymes in situ in cells or in vitro in cell extracts. Preferred heterologous host cells for production of the instant isoflavone biosynthetic enzymes are microbial hosts. Microbial expression systems and expression vectors containing regulatory sequences that direct high level expression of foreign proteins are well known to those skilled in the art. Any of these could be used to construct chimeric genes for production of the instant isoflavone biosynthetic enzymes. These chimeric genes could then be introduced into appropriate microorganisms via transformation to provide high level expression of the enzymes. An example of a vector for high level expression of the instant isoflavone biosynthetic enzymes in a bacterial host is provided (Example 5).

All or a portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) Genomics 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al.,(1980) Am. J. Hum. Genet.32:314–33 1).

For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) Genomics 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) Am. J. Hum. Genet.32:314–331).

The production and use of plant gene-derived probes for use in genetic mapping is described in R. Bernatzky, R. and Tanksley, S. D. (1986) Plant Mol. Biol. Reporter 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: Nonmammalian Genomic Analysis: A Practical Guide, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991 ) Trends Genet. 7:149–154). Although current methods of FISH mapping favor use of large clones (several to several hundred KB; see Laan, M. et al. (1995) Genome Research 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) J. Lab. Clin. Med. 114(2):95–96), polymorphism of PCR-amplified fragments (CAPS; Sheffield, V. C. et al. (1993) Genomics 16:325–332), allele-specific ligation (Landegren, U. et al. (1988) Science 241:1077–1080), nucleotide extension reactions (Sokolov, B. P. (1990) Nucleic Acid Res. 18:3671), Radiation Hybrid Mapping (Walter, M. A. et al. (1997) Nature Genetics 7:22–28) and Happy Mapping (Dear, P. H. and Cook, P. R. (1989) Nucleic Acid Res. 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clone encoding chalcone isomerase either by targeted gene disruption protocols or by identifying specific mutants for these genes contained in a maize population carrying mutations in all possible genes (Ballinger and Benzer, (1989) Proc. Natl. Acad. Sci USA 86:9402; Koes et al., (1995) Proc. Natl. Acad. Sci USA 92:8149; Bensen et al., (1995) Plant Cell 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the genes encoding the plant chalcone isomerase. Alternatively, the instant nucleic acid fragments may be used as hybridization probes against PCR amplification products generated from the mutation population using the mutation tag sequence primer in conjunction with an arbitrary genomic site primer, such as that for a restriction enzyme site-anchored synthetic adaptor. With either method, a plant containing a mutation in the chalcone isomerase gene can be identified and obtained. This mutant plant can then be used to determine or confirm the natural function of the plant gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of he invention to adapt it to various usages and conditions.

Example 1

Composition of cDNA Libraries; Isolation and Sequencing of cDNA Clones cDNA libraries representing mRNAs from various soybean tissues were prepared. The characteristics of the libraries are described below.

TABLE 2 cDNA Libraries from Soybean

| Library | Tissue | Clone |
|---|---|---|
| se3 | Soybean Embryo 13 Days After Flowering | se3.pk0034.g5 |
| sre | Soybean Root, Elongation Zone | sre.pk0016.c8 |
| ssm | Soybean Shoot Meristem | ssm.pk0013.e3 | cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification and Characterization of cDNA Clones

ESTs encoding soybean isoflavone biosynthetic enzymes were identified by conducting BLAST (Basic Local Alignment Search Tool; Altschul, S. F., et al., (1993) J. Mol. Biol. 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using the nucleotide sequence from clone ssm.pk0013.e3 revealed similarity of the protein encoded by the cDNA to *Pueraria lobata* chalcone flavanone isomerase (DDJB Accession No. D63577; pLog=71.37). The sequence of the entire cDNA insert in clone ssm.pk0013.e3 was determined and is set forth in SEQ ID NO:1; the deduced amino acid sequence of this cDNA is shown in SEQ ID NO:2. The entire cDNA insert in clone ssm.pk0013.e3 was reevaluated by BLAST, yielding an even higher pLog value vs. the Pueraria lobata chalcone flavanone isomerase (D63577; pLog=126.29). Sequence alignments and BLAST scores and probabilities indicate that the instant nucleic acid fragment encodes the entire soybean chalcone isomerase enzyme. This is the first soybean EST identified for chalcone isomerase.

The BLASTX search using the nucleotide sequence from clone se3.pk0034.g5 revealed similarity of the protein encoded by the cDNA to *Lupinus albus* isoflavone reductase-like protein (GenBank Accession No. U48590; pLog=68.24). The sequence of the entire cDNA insert in clone se3.pk0034.g5 was determined and is set forth in SEQ ID NO:4; the deduced amino acid sequence of this cDNA is shown in SEQ ID NO:5. The entire cDNA insert in clone se3.pk0034.g5 was reevaluated by BLAST, yielding an even higher pLog value vs. an isoflavone reductase homolog from *Lupinus albus* (SWISS-PROT Accession No. P52581; pLog=171.54). Sequence alignments and BLAST scores and probabilities indicate that the instant nucleic acid fragment encodes the entire soybean isoflavone reductase enzyme. This is the first soybean EST identified for isoflavone reductase.

The BLASTX search using the nucleotide sequence from clone sre.pk0016.c8 revealed similarity of the protein encoded by the cDNA to *Medicago sativa* vestitone reductase (GenBank Accession No. U28213; pLog=52.57). The sequence of the entire cDNA insert in clone sre.pk0016.c8 was determined and is set forth in SEQ ID NO:7; the deduced amino acid sequence of this cDNA is shown in SEQ ID NO:8. The entire cDNA insert in clone sre.pk0016.c8 was reevaluated by BLAST, yielding an even higher pLog value vs. the *Medicago sativa* vestitone reductase (U28213; pLog=170.39). Sequence alignments and BLAST scores and probabilities indicate that the instant nucleic acid fragment encodes the entire soybean vestitone reductase enzyme. This is the first soybean EST identified for vestitone reductase.

Example 3

Expression of Chimeric Genes in Monocot Cells

A chimeric gene comprising a cDNA encoding an isoflavone biosynthetic enzyme, for example chalcone isomerase in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Boulevard, Manassas, Va. 20110), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U. S. Biochemical). The resulting plasmid construct would comprise a chimeric gene encoding, in the 5' to 3' direction, the maize 27 kD zein promoter, a cDNA fragment encoding a soybean isoflavone biosynthetic enzyme, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 4

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant soybean isoflavone biosynthetic enzymes in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

A cDNA fragment encoding any of the instant soybean isoflavone biosynthetic enzymes may be generated by polymerase chain reaction (PCR) of the appropriate cDNA clones using appropriate oligonucleotide primers. Cloning sites can be incorporated into the oligonucleotides to provide proper orientation of the amplified DNA fragment when inserted into the expression vector. Amplification is then performed in a standard PCR, and the isolated fragment is inserted into a pUC18 vector carrying the seed expression cassette.

Soybean embroys may then be transformed with the expression vector comprising sequences encoding a soybean isoflavone biosynthetic enzyme. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) *Nature* (London) 327:70, U.S. Pat. No. 4,945,050). A Du Pont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli;* Gritz et al.(1 983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the biosynthetic enzyme and the phaseolin 3' region can be isolated as a restriction fragment. This fragment can then be inserted into a unique restriction site of the vector carrying the marker gene.

To 50 $\mu$L of a 60 mg/mL 1 $\mu$m gold particle suspension is added (in order): 5 $\mu$L DNA (1 $\mu$g/$\mu$L), 20 $\mu$l spermidine (0.1 M), and 50 $\mu$L CaCl$_2$ (2.5 M). The particle preparation is then agitated for three minutes, spun in a microfuge for 10 seconds and the supernatant removed. The DNA-coated particles are then washed once in 400 $\mu$L 70% ethanol and resuspended in 40 $\mu$L of anhydrous ethanol. The DNA/particle suspension can be sonicated three times for one second each. Five $\mu$L of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 5

Expression of Chimeric Genes in Microbial Cells

The nucleic acid fragments encoding the instant soybean isoflavone biosynthetic enzymes can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the enzyme. This fragment may then be purified on a 1% NuSieve GTG™ low melting agarose gel (FMC). Buffer and agarose contain 10 $\mu$g/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 $\mu$L of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as decribed above. The prepared vector pBT430 and fragment can then be ligated at 16° C. for 15 hours followed by transformation into DH5 electrocompetent cells (GIBCO BRL). Transformants can be selected on agar plates containing LB media and 100 $\mu$g/mL ampicillin. Transformants containing the gene encoding the enzyme are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-$\beta$-galactoside, the inducer) can be added to a final concentration of 0.4 mM and incubation can be continued for 3 h at 25°. Cells are then harvested by centrifugation and re-suspended in 50 $\mu$L of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One $\mu$g of protein from the soluble fraction of the culture can be separated by SDS-polyacrylamide gel electrophoresis. Gels can be observed for protein bands migrating at the expected molecular weight.

What is claimed is:

1. An isolated polynucleotide that encodes an isoflavone reductase polypeptide having a sequence identity of at least 90% when compared to a polypeptide set forth in SEQ ID NO:5.

2. A polynucleotide sequence of claim 1, wherein the sequence identity is at least 95%.

3. The polynucleotide of claim 1 wherein the polynucleotide encodes a polypeptide set forth in SEQ ID NO:5.

4. The polynucleotide of claim 1, wherein the polynucleotide comprises a nucleotide sequence set forth in SEQ ID NO:4.

5. An isolated complement of the polynucleotide of claim 1, wherein (a) the complement and the polynucleotide consist of the same number of nucleotides, and (b) the nucleotide sequences of the complement and the polynucleotide have 100% complementarity.

6. An isolated polynucleotide that encodes an isoflavone reductase polypeptide and that remains hybridized with the isolated polynucleotide of claim 4 under a wash condition of 0.1×SSC, 0.1% SDS, and 65° C.

7. A cell comprising the polynucleotide of claim 1.

8. The cell of claim 7, wherein the cell is selected from the group consisting of a yeast cell, a bacterial cell and a plant cell.

9. A method for transforming a cell comprising introducing into a cell the polynucleotide of claim 1.

10. A chimeric nucleic acid molecule comprising the polynucleotide of claim 1 operably linked to at least one suitable regulatory sequence.

11. A method for altering the level of isoflavone reductase expression in a host cell, the method comprising:

(a) transforming a host cell with the chimeric nucleic acid molecule of claim 10; and (b) growing the transformed cell obtained in step (a) under conditions suitable for the expression of the chimeric nucleic acid molecule.

* * * * *

UNITED STATES PATENT AND TRADEMARK OFFICE
CERTIFICATE OF CORRECTION

PATENT NO.    : 6,521,433 B1
DATED         : February 18, 2003
INVENTOR(S)   : Fader Gary M.

It is certified that error appears in the above-identified patent and that said Letters Patent is hereby corrected as shown below:

<u>Column 37,</u>
Line 14, delete "sequence".

Signed and Sealed this

Thirty-first Day of August, 2004

JON W. DUDAS
*Director of the United States Patent and Trademark Office*

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 846 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 40..693

(xi) SEQUENCE DESCRIPTION: SEQ ID NO:1:

```
AATTCGGCAC GAGGTTAAAT AGAAAAGAGG AGTTTGAGA ATG GCA ACG ATC AGC            54
                                           Met Ala Thr Ile Ser
                                             1               5

GCG GTT CAG GTG GAG TTC CTG GAG TTT CCA GCG GTG GTT ACT TCA CCA         102
Ala Val Gln Val Glu Phe Leu Glu Phe Pro Ala Val Val Thr Ser Pro
             10                  15                  20

GCC TCC GGC AAG ACC TAT TTC CTC GGC GGC GCA GGG GAG AGA GGA TTG         150
Ala Ser Gly Lys Thr Tyr Phe Leu Gly Gly Ala Gly Glu Arg Gly Leu
                 25                  30                  35

ACG ATT GAG GGG AAG TTC ATA AAG TTC ACA GGC ATA GGA GTA TAC TTG         198
Thr Ile Glu Gly Lys Phe Ile Lys Phe Thr Gly Ile Gly Val Tyr Leu
             40                  45                  50

GAG GAT AAG GCG GTG CCA TCA CTC GCC GCT AAG TGG AAG GGT AAA ACT         246
Glu Asp Lys Ala Val Pro Ser Leu Ala Ala Lys Trp Lys Gly Lys Thr
         55                  60                  65

TCA GAG GAG TTA GTT CAC ACC CTC CAC TTC TAC AGG GAT ATC ATT TCA         294
Ser Glu Glu Leu Val His Thr Leu His Phe Tyr Arg Asp Ile Ile Ser
 70                  75                  80                  85

GGG CCG TTT GAA AAG CTA ATT AGA GGG TCG AAG ATT CTG CCA TTG GCT         342
Gly Pro Phe Glu Lys Leu Ile Arg Gly Ser Lys Ile Leu Pro Leu Ala
                 90                  95                 100

GGC GCT GAA TAC TCA AAG AAG GTG ATG GAA AAC TGC GTG GCA CAC ATG         390
Gly Ala Glu Tyr Ser Lys Lys Val Met Glu Asn Cys Val Ala His Met
             105                 110                 115

AAG TCT GTT GGG ACT TAC GGT GAT GCT GAA GCC GCA GCC ATT GAA AAG         438
Lys Ser Val Gly Thr Tyr Gly Asp Ala Glu Ala Ala Ala Ile Glu Lys
                 120                 125                 130

TTT GCT GAA GCC TTC AAG AAT GTG AAT TTT GCA CCT GGT GCC TCT GTT         486
Phe Ala Glu Ala Phe Lys Asn Val Asn Phe Ala Pro Gly Ala Ser Val
             135                 140                 145

TTC TAC AGA CAA TCA CCT GAT GGA ATC TTG GGG CTT AGT TTC TCT GAA         534
Phe Tyr Arg Gln Ser Pro Asp Gly Ile Leu Gly Leu Ser Phe Ser Glu
150                 155                 160                 165

GAT GCA ACA ATA CCA GAA AAG GAG GCT GCA GTG ATA GAG AAC AAG GCT         582
Asp Ala Thr Ile Pro Glu Lys Glu Ala Ala Val Ile Glu Asn Lys Ala
                 170                 175                 180

GTA TCA GCG GCG GTC TTG GAG ACC ATG ATT GGT GAA CAT GCT GTT TCC         630
Val Ser Ala Ala Val Leu Glu Thr Met Ile Gly Glu His Ala Val Ser
             185                 190                 195

CCT GAC TTA AAA CGC AGT TTG GCT TCT CGA TTG CCT GCG GTA TTG AGC         678
Pro Asp Leu Lys Arg Ser Leu Ala Ser Arg Leu Pro Ala Val Leu Ser
         200                 205                 210
```

```
CAC GGC ATT ATA GTC TGAGAAATGA GAAGGATCAA CTTTACCTTT TTCAAATATT    733
His Gly Ile Ile Val
    215

CTTGTTTTTC TCCTTTCTTT CTTGTCGCTT GTCATGTATT TCTACTGTTT TATTAAATAA   793

TAAAATTGAG TTCTGTTAGA GTTGGTGAAA AAAAAAAAAA AAAAAAAACT CGA          846
```

(2) INFORMATION FOR SEQ ID NO:2:

(i) SEQUENCE CHARACTERISTICS:
        (A) LENGTH: 218 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Thr Ile Ser Ala Val Gln Val Glu Phe Leu Glu Phe Pro Ala
 1               5                  10                  15

Val Val Thr Ser Pro Ala Ser Gly Lys Thr Tyr Phe Leu Gly Gly Ala
                20                  25                  30

Gly Glu Arg Gly Leu Thr Ile Glu Gly Lys Phe Ile Lys Phe Thr Gly
            35                  40                  45

Ile Gly Val Tyr Leu Glu Asp Lys Ala Val Pro Ser Leu Ala Ala Lys
     50                  55                  60

Trp Lys Gly Lys Thr Ser Glu Glu Leu Val His Thr Leu His Phe Tyr
 65                  70                  75                  80

Arg Asp Ile Ile Ser Gly Pro Phe Glu Lys Leu Ile Arg Gly Ser Lys
                85                  90                  95

Ile Leu Pro Leu Ala Gly Ala Glu Tyr Ser Lys Lys Val Met Glu Asn
            100                 105                 110

Cys Val Ala His Met Lys Ser Val Gly Thr Tyr Gly Asp Ala Glu Ala
        115                 120                 125

Ala Ala Ile Glu Lys Phe Ala Glu Ala Phe Lys Asn Val Asn Phe Ala
    130                 135                 140

Pro Gly Ala Ser Val Phe Tyr Arg Gln Ser Pro Asp Gly Ile Leu Gly
145                 150                 155                 160

Leu Ser Phe Ser Glu Asp Ala Thr Ile Pro Glu Lys Glu Ala Ala Val
                165                 170                 175

Ile Glu Asn Lys Ala Val Ser Ala Ala Val Leu Glu Thr Met Ile Gly
            180                 185                 190

Glu His Ala Val Ser Pro Asp Leu Lys Arg Ser Leu Ala Ser Arg Leu
        195                 200                 205

Pro Ala Val Leu Ser His Gly Ile Ile Val
    210                 215
```

(2) INFORMATION FOR SEQ ID NO:3:

(i) SEQUENCE CHARACTERISTICS:
        (A) LENGTH: 224 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

```
Met Ala Ala Ala Ala Ala Val Ala Thr Ile Ser Ala Val Gln Val Glu
 1               5                  10                  15

Phe Leu Glu Phe Pro Ala Val Val Thr Ser Pro Ala Ser Gly Arg Thr
```

```
                    20                  25                  30
Tyr Phe Leu Gly Gly Ala Gly Glu Arg Gly Leu Thr Ile Glu Gly Lys
            35                  40                  45

Phe Ile Lys Phe Thr Gly Ile Gly Val Tyr Leu Glu Asp Lys Ala Val
 50                  55                  60

Ser Ser Leu Ala Ala Lys Trp Lys Gly Lys Pro Ser Glu Glu Leu Val
 65                  70                  75                  80

Glu Thr Leu Asp Phe Tyr Arg Asp Ile Ile Ser Gly Pro Phe Glu Lys
                 85                  90                  95

Leu Ile Arg Gly Ser Lys Ile Leu Pro Leu Ser Gly Val Glu Tyr Ser
            100                 105                 110

Lys Lys Val Met Glu Asn Cys Val Ala His Met Lys Ser Val Gly Thr
        115                 120                 125

Tyr Gly Asp Ala Glu Ala Ala Ile Glu Lys Phe Ala Glu Ala Phe
    130                 135                 140

Lys Asn Val Asn Phe Gln Pro Gly Ala Thr Val Phe Tyr Arg Gln Ser
145                 150                 155                 160

Pro Asp Gly Val Leu Gly Leu Ser Phe Ser Glu Asp Val Thr Ile Pro
                165                 170                 175

Asp Asn Glu Ala Ala Val Ile Glu Asn Lys Ala Val Ser Ala Ala Val
            180                 185                 190

Leu Glu Thr Met Ile Gly Glu His Ala Val Ser Pro Asp Leu Lys Arg
        195                 200                 205

Ser Leu Ala Ser Arg Leu Pro Ala Val Leu Ser His Gly Ile Ile Val
210                 215                 220
```

(2) INFORMATION FOR SEQ ID NO:4:

(i) SEQUENCE CHARACTERISTICS:
        (A) LENGTH: 1223 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 55..1223

(ix) FEATURE:
        (A) NAME/KEY: CDS
        (B) LOCATION: 55..990

(xi) SEQUENCE DESCRIPTION: SEQ ID NO:4:

```
AATTCGGCAC GAGGAAGAAC CAACAAGAGG GGTATTGAGA TTGAGATTCA AGTA ATG      57
                                                            Met
                                                             1

GGG AAG AGC AAG GTT CTT GTG GTG GGG GGA ACT GGG TAC ATA GGG AGG     105
Gly Lys Ser Lys Val Leu Val Val Gly Gly Thr Gly Tyr Ile Gly Arg
         5                  10                  15

AGG ATA GTG AGG GCA AGC CTG GCA CTG GGC CAT GAG ACC TAT GTG GTT    153
Arg Ile Val Arg Ala Ser Leu Ala Leu Gly His Glu Thr Tyr Val Val
             20                  25                  30

CAG AGG CCA GAG TTG AGC CTC CAG ATA GAG AAG CTG CAG AGG CTC CTC    201
Gln Arg Pro Glu Leu Ser Leu Gln Ile Glu Lys Leu Gln Arg Leu Leu
         35                  40                  45

TCC TTC AAG AAG CAA GGT GCT CAT CTC ATT GAG GCC TCT TTC AAT GAT    249
Ser Phe Lys Lys Gln Gly Ala His Leu Ile Glu Ala Ser Phe Asn Asp
 50                  55                  60                  65
```

```
CAC AAG AGC CTT GTT GAT GCT GTG AAG CAG GTT GAT GTT GTC ATC AGT      297
His Lys Ser Leu Val Asp Ala Val Lys Gln Val Asp Val Val Ile Ser
                 70                  75                  80

GCC ATC TCT GGT GTT CAC ATC AGG AGC CAC AGC ATC ACT CTG CAA CTC      345
Ala Ile Ser Gly Val His Ile Arg Ser His Ser Ile Thr Leu Gln Leu
             85                  90                  95

AAA CTT GTT GAG GCC ATC AAA GAA GCT GGG AAC GTT AAG CGT TTC TTG      393
Lys Leu Val Glu Ala Ile Lys Glu Ala Gly Asn Val Lys Arg Phe Leu
            100                 105                 110

CCT TCT GAA TTT GGC CTA GAC CCA GCA AGG ATG GGG CAT GCA TTA GAA      441
Pro Ser Glu Phe Gly Leu Asp Pro Ala Arg Met Gly His Ala Leu Glu
        115                 120                 125

CCA GGA AGG GTA ACA TTT GAA GAC AAA ATG GCT GTA AGG AAA CCA ATA      489
Pro Gly Arg Val Thr Phe Glu Asp Lys Met Ala Val Arg Lys Pro Ile
130                 135                 140                 145

GAG GAA GCT AAT ATC CCT TTC ACT TAC ATC TCC GCA AAC CTC TTT GCT      537
Glu Glu Ala Asn Ile Pro Phe Thr Tyr Ile Ser Ala Asn Leu Phe Ala
                150                 155                 160

GGA TAC TTT GCT GGC AGC CTC TCT CAG ATG GGG TCT TTT GTG CCA CCA      585
Gly Tyr Phe Ala Gly Ser Leu Ser Gln Met Gly Ser Phe Val Pro Pro
            165                 170                 175

AGG GAC AAG GTG CAT CTC TTT GGA GAT GGC ACA CTC AAA GCT ATT TTT      633
Arg Asp Lys Val His Leu Phe Gly Asp Gly Thr Leu Lys Ala Ile Phe
        180                 185                 190

CTG GAT GAA GAT GAT GTT GCA ACA TAT ACA ATC AAG GCA ATA GAT GAT      681
Leu Asp Glu Asp Asp Val Ala Thr Tyr Thr Ile Lys Ala Ile Asp Asp
    195                 200                 205

CCA CGA ACC CTT AAC AAA ACA TTG TAC CTA AGG CCT CCA GAA AAT ATT      729
Pro Arg Thr Leu Asn Lys Thr Leu Tyr Leu Arg Pro Pro Glu Asn Ile
210                 215                 220                 225

ATC TTT CAA GCA GAG CTT ATT GGA ATT TGG GAG AAA CTT ATT GGA AAG      777
Ile Phe Gln Ala Glu Leu Ile Gly Ile Trp Glu Lys Leu Ile Gly Lys
                230                 235                 240

GAA CTA GAG AAG ACA TAC ATA CCT CCA GAA GGC TTT CTT ACA ACA CTG      825
Glu Leu Glu Lys Thr Tyr Ile Pro Pro Glu Gly Phe Leu Thr Thr Leu
            245                 250                 255

AAA GGG TTG GAT TAT AAA CTT CAA GTA GGG ATT GGA CAC TTT TAT CAT      873
Lys Gly Leu Asp Tyr Lys Leu Gln Val Gly Ile Gly His Phe Tyr His
        260                 265                 270

ATA TTC TAC GAG GGA TGT TTA GCA AAT TTT GAA ATT GGA GAG GAA GGA      921
Ile Phe Tyr Glu Gly Cys Leu Ala Asn Phe Glu Ile Gly Glu Glu Gly
    275                 280                 285

GAA GAA GCA TCC AAG CTT TAC CCT GAA GTG AAT TAC ACA CGC ATG GAC      969
Glu Glu Ala Ser Lys Leu Tyr Pro Glu Val Asn Tyr Thr Arg Met Asp
290                 295                 300                 305

GAG TAC CTA AAA ATT TAT GTG TAAAAGGAAC TCATTCAGTA GGAGTTCAGT        1020
Glu Tyr Leu Lys Ile Tyr Val
                310

GATTCAAACA GGAACACGGT TTTTAGCTAC AATAACCTTA ATTTAAGGAG ATGATTTTGT   1080

GCTTATAATT CGATGGGGAA ACTGGATTTT TCGGATCTTG AAATGTGAAC GAGTTTAACT   1140

TTATCATTAA TTTAAGCTCT GTTGTTTTA AAAAAAAAA AAAAAAAAAA AAAAAAAAA     1200

AAAAAAAAAA AAAAAAACT CGA                                           1223

(2) INFORMATION FOR SEQ ID NO:5:

(i) SEQUENCE CHARACTERISTICS:
        (A) LENGTH: 312 amino acids
        (B) TYPE: amino acid
        (D) TOPOLOGY: linear
```

(ii) MOLECULE TYPE: protein (xi) SEQUENCE DESCRIPTION: SEQ ID NO:5:

```
Met Gly Lys Ser Lys Val Leu Val Val Gly Gly Thr Gly Tyr Ile Gly
 1               5                  10                  15

Arg Arg Ile Val Arg Ala Ser Leu Ala Leu Gly His Glu Thr Tyr Val
                20                  25                  30

Val Gln Arg Pro Glu Leu Ser Leu Gln Ile Glu Lys Leu Gln Arg Leu
            35                  40                  45

Leu Ser Phe Lys Lys Gln Gly Ala His Leu Ile Glu Ala Ser Phe Asn
        50                  55                  60

Asp His Lys Ser Leu Val Asp Ala Val Lys Gln Val Asp Val Val Ile
 65                 70                  75                  80

Ser Ala Ile Ser Gly Val His Ile Arg Ser His Ser Ile Thr Leu Gln
                85                  90                  95

Leu Lys Leu Val Glu Ala Ile Lys Glu Ala Gly Asn Val Lys Arg Phe
            100                 105                 110

Leu Pro Ser Glu Phe Gly Leu Asp Pro Ala Arg Met Gly His Ala Leu
        115                 120                 125

Glu Pro Gly Arg Val Thr Phe Glu Asp Lys Met Ala Val Arg Lys Pro
130                 135                 140

Ile Glu Glu Ala Asn Ile Pro Phe Thr Tyr Ile Ser Ala Asn Leu Phe
145                 150                 155                 160

Ala Gly Tyr Phe Ala Gly Ser Leu Ser Gln Met Gly Ser Phe Val Pro
                165                 170                 175

Pro Arg Asp Lys Val His Leu Phe Gly Asp Gly Thr Leu Lys Ala Ile
            180                 185                 190

Phe Leu Asp Glu Asp Asp Val Ala Thr Tyr Thr Ile Lys Ala Ile Asp
        195                 200                 205

Asp Pro Arg Thr Leu Asn Lys Thr Leu Tyr Leu Arg Pro Pro Glu Asn
210                 215                 220

Ile Ile Phe Gln Ala Glu Leu Ile Gly Ile Trp Glu Lys Leu Ile Gly
225                 230                 235                 240

Lys Glu Leu Glu Lys Thr Tyr Ile Pro Pro Glu Gly Phe Leu Thr Thr
                245                 250                 255

Leu Lys Gly Leu Asp Tyr Lys Leu Gln Val Gly Ile Gly His Phe Tyr
            260                 265                 270

His Ile Phe Tyr Glu Gly Cys Leu Ala Asn Phe Glu Ile Gly Glu Glu
        275                 280                 285

Gly Glu Glu Ala Ser Lys Leu Tyr Pro Glu Val Asn Tyr Thr Arg Met
290                 295                 300

Asp Glu Tyr Leu Lys Ile Tyr Val
305                 310
```

(2) INFORMATION FOR SEQ ID NO:6:

(i) SEQUENCE CHARACTERISTICS:
        (A) LENGTH: 312 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

Met Gly Lys Ser Lys Val Leu Val Val Gly Gly Thr Gly Tyr Val Gly

```
              1               5                  10                 15
            Arg Arg Ile Val Lys Ala Ser Leu Glu His Gly His Glu Thr Phe Ile
                            20                  25                 30

Leu Gln Arg Pro Glu Ile Gly Leu Asp Ile Glu Lys Leu Gln Ile Leu
                            35                  40                 45

Leu Ser Phe Lys Lys Gln Gly Ala Ile Leu Val Glu Ala Ser Phe Ser
                            50                  55                 60

Asp His Lys Ser Leu Val Asp Ala Val Lys Leu Val Asp Val Val Ile
            65                              70              75                 80

Cys Thr Met Ser Gly Val His Phe Arg Ser His Asn Leu Leu Thr Gln
                            85                  90                 95

Leu Lys Leu Val Glu Ala Ile Lys Asp Ala Gly Asn Ile Lys Arg Phe
                            100                 105                110

Leu Pro Ser Glu Phe Gly Met Asp Pro Ala Leu Met Gly His Ala Leu
                            115                 120                125

Glu Pro Gly Arg Val Thr Phe Asp Glu Lys Met Thr Val Arg Lys Ala
                            130                 135                140

Ile Glu Glu Ala Asn Ile Pro Phe Thr Tyr Ile Ser Ala Asn Cys Phe
            145                             150                 155                160

Ala Gly Tyr Phe Ala Gly Asn Leu Ser Gln Met Lys Thr Leu Leu Pro
                            165                 170                175

Pro Arg Asp Lys Val Leu Leu Tyr Gly Asp Gly Asn Val Lys Pro Val
                            180                 185                190

Tyr Met Asp Glu Asp Val Ala Thr Tyr Thr Ile Lys Thr Ile Asp
                            195                 200                205

Asp Pro Arg Thr Leu Asn Lys Thr Val Tyr Leu Arg Pro Pro Glu Asn
                            210                 215                220

Ile Leu Thr His Lys Glu Leu Ile Glu Lys Trp Glu Leu Ile Gly
            225                             230                 235                240

Lys Gln Leu Glu Lys Asn Ser Ile Ser Glu Lys Asp Phe Leu Ser Thr
                            245                 250                255

Leu Lys Gly Leu Asp Phe Ala Ser Gln Val Gly Val Gly His Phe Tyr
                            260                 265                270

His Ile Phe Tyr Glu Gly Cys Leu Thr Asn Phe Glu Ile Gly Glu Asn
                            275                 280                285

Gly Glu Glu Ala Ser Glu Leu Tyr Pro Glu Val Asn Tyr Thr Arg Met
                            290                 295                300

Asp Gln Tyr Leu Lys Val Tyr Val
            305                             310

(2) INFORMATION FOR SEQ ID NO:7:

(i) SEQUENCE CHARACTERISTICS:
             (A) LENGTH:  1218 base pairs
             (B) TYPE:  nucleic acid
             (C) STRANDEDNESS:  single
             (D) TOPOLOGY:  linear (ii) MOLECULE TYPE:  cDNA (ix) FEATURE:
             (A) NAME/KEY:  CDS
             (B) LOCATION:  48..1028

(xi) SEQUENCE DESCRIPTION:  SEQ ID NO:7:

AATTCGGCAC GAGGAAAAGT AAACACTGCC ACAGCAAGAG TGTTCAA ATG GGA GAG        56
                                                          Met Gly Glu
                                                            1
```

-continued

```
GGA AAA GGA AGA ATT TGT GTC ACT GGA GGC ACA GGA TTC CTT GGT TCA        104
Gly Lys Gly Arg Ile Cys Val Thr Gly Gly Thr Gly Phe Leu Gly Ser
     5              10                  15

TGG ATA ATC AAG AGC CTC CTT GAA CAT GGA TAT GCT GTT AAT ACC ACT        152
Trp Ile Ile Lys Ser Leu Leu Glu His Gly Tyr Ala Val Asn Thr Thr
 20              25                  30                  35

ATA AGA TCT GAC CCA GGA CGC AAG AGA GAT GTT AGC TTC CTC ACA AAC        200
Ile Arg Ser Asp Pro Gly Arg Lys Arg Asp Val Ser Phe Leu Thr Asn
                 40                  45                  50

CTA CCT GGT GCA TCA GAA AAG CTT AAA ATT TTC AAC GCT GAT CTC AGC        248
Leu Pro Gly Ala Ser Glu Lys Leu Lys Ile Phe Asn Ala Asp Leu Ser
                     55                  60                  65

GAC CCA GAG AGT TTT GGT CCA GCA GTT GAG GGT TGT GTT GGA ATT TTT        296
Asp Pro Glu Ser Phe Gly Pro Ala Val Glu Gly Cys Val Gly Ile Phe
         70                  75                  80

CAC ACT GCC ACC CCA ATT GAT TTT GCG GTG AAC GAG CCA GAG GAA GTG        344
His Thr Ala Thr Pro Ile Asp Phe Ala Val Asn Glu Pro Glu Glu Val
             85                  90                  95

GTG ACC AAA AGA GCC ATT GAT GGA GCA CTA GGC ATA TTG AAA GCA GGC        392
Val Thr Lys Arg Ala Ile Asp Gly Ala Leu Gly Ile Leu Lys Ala Gly
100                 105                 110                 115

CTA AAA GCA AAG ACT GTG AAG AGG GTT GTT TAC ACT TCT AGC GCC TCC        440
Leu Lys Ala Lys Thr Val Lys Arg Val Val Tyr Thr Ser Ser Ala Ser
                    120                 125                 130

ACT GTT TCC TTC AGC AGC CTA GAA GAG AAA GAT GTG GTG GAT GAG AGT        488
Thr Val Ser Phe Ser Ser Leu Glu Glu Lys Asp Val Val Asp Glu Ser
                135                 140                 145

GTT TGG AGT GAT GTG GAT TTG CTC AGG AGT GTG AAG CCT TTT AGT TGG        536
Val Trp Ser Asp Val Asp Leu Leu Arg Ser Val Lys Pro Phe Ser Trp
            150                 155                 160

TCC TAT GCA GTT TCA AAG GTG TTG TCA GAG AAG GCA GTG CTT GAA TTT        584
Ser Tyr Ala Val Ser Lys Val Leu Ser Glu Lys Ala Val Leu Glu Phe
        165                 170                 175

GGA GAA CAG AAT GGA TTG GAA GTT ACC ACT CTT GTG CTT CCT TTT GTT        632
Gly Glu Gln Asn Gly Leu Glu Val Thr Thr Leu Val Leu Pro Phe Val
180                 185                 190                 195

GTT GGA CGC TTT GTT TGT CCC AAG CTT CCT GAT TCT GTT GAA AGA GCA        680
Val Gly Arg Phe Val Cys Pro Lys Leu Pro Asp Ser Val Glu Arg Ala
                    200                 205                 210

CTG CTT TTG GTG TTA GGC AAA AAG GAA GAA ATT GGT GTC ATT CGT TAC        728
Leu Leu Leu Val Leu Gly Lys Lys Glu Glu Ile Gly Val Ile Arg Tyr
                215                 220                 225

CAT ATG GTA CAT GTG GAT GAT GTG GCT AGA GCA CAT ATC TTC CTG CTT        776
His Met Val His Val Asp Asp Val Ala Arg Ala His Ile Phe Leu Leu
            230                 235                 240

GAG CAT CCT AAC CCA AAA GGG AGA TAT AAT TGC TCA CCA TTC ATT GTG        824
Glu His Pro Asn Pro Lys Gly Arg Tyr Asn Cys Ser Pro Phe Ile Val
        245                 250                 255

CCT ATT GAA GAG ATT GCT GAA ATT ATT TCA GCC AAA TAC CCA GAA TAT        872
Pro Ile Glu Glu Ile Ala Glu Ile Ile Ser Ala Lys Tyr Pro Glu Tyr
260                 265                 270                 275

CAA ATA CCA GCA CTA GAA GAG GTG AAG GAA ATT AAA GGT GCC AAG TTA        920
Gln Ile Pro Ala Leu Glu Glu Val Lys Glu Ile Lys Gly Ala Lys Leu
                    280                 285                 290

CCA CAT TTA ACC TCC CAG AAA CTT GTG GAT GCT GGT TTT GAG TTC AAG        968
Pro His Leu Thr Ser Gln Lys Leu Val Asp Ala Gly Phe Glu Phe Lys
                295                 300                 305

TAT AGC GTT GAG GAC ATA TTT ACG GAT GCA ATT GAA TGC TGC AAG GAA       1016
Tyr Ser Val Glu Asp Ile Phe Thr Asp Ala Ile Glu Cys Cys Lys Glu
```

-continued

```
            310                 315                 320
AAG GGT TAC CTT TAATCGATTT TAGCCACGAA GTTGAAAAAA TAAAATTGTC       1068
Lys Gly Tyr Leu
325

GAAGATGATT GTTAGTTCGT ACTATTTTCA GATCCCTGGC AATGATGCCT CTTGACATGT 1128

ACTCCATTTA ATGCATGATG TTTTCTTAAT AAATTGACCA GGGAAATAAT TCTTTTGGTT 1188

TGTCTGAAAA AAAAAAAAAA AAAAACTCGA                                 1218
```

(2) INFORMATION FOR SEQ ID NO:8:

(i) SEQUENCE CHARACTERISTICS:
        (A) LENGTH: 327 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gly Glu Gly Lys Gly Arg Ile Cys Val Thr Gly Thr Gly Phe
1               5                   10                  15

Leu Gly Ser Trp Ile Ile Lys Ser Leu Leu Glu His Gly Tyr Ala Val
            20                  25                  30

Asn Thr Thr Ile Arg Ser Asp Pro Gly Arg Lys Arg Asp Val Ser Phe
            35                  40                  45

Leu Thr Asn Leu Pro Gly Ala Ser Glu Lys Leu Lys Ile Phe Asn Ala
        50                  55                  60

Asp Leu Ser Asp Pro Glu Ser Phe Gly Pro Ala Val Glu Gly Cys Val
65                  70                  75                  80

Gly Ile Phe His Thr Ala Thr Pro Ile Asp Phe Ala Val Asn Glu Pro
                85                  90                  95

Glu Glu Val Val Thr Lys Arg Ala Ile Asp Gly Ala Leu Gly Ile Leu
            100                 105                 110

Lys Ala Gly Leu Lys Ala Lys Thr Val Lys Arg Val Val Tyr Thr Ser
        115                 120                 125

Ser Ala Ser Thr Val Ser Phe Ser Ser Leu Glu Glu Lys Asp Val Val
    130                 135                 140

Asp Glu Ser Val Trp Ser Asp Val Asp Leu Leu Arg Ser Val Lys Pro
145                 150                 155                 160

Phe Ser Trp Ser Tyr Ala Val Ser Lys Val Leu Ser Glu Lys Ala Val
                165                 170                 175

Leu Glu Phe Gly Glu Gln Asn Gly Leu Glu Val Thr Thr Leu Val Leu
            180                 185                 190

Pro Phe Val Val Gly Arg Phe Val Cys Pro Lys Leu Pro Asp Ser Val
        195                 200                 205

Glu Arg Ala Leu Leu Leu Val Leu Gly Lys Lys Glu Glu Ile Gly Val
    210                 215                 220

Ile Arg Tyr His Met Val His Val Asp Val Ala Arg Ala His Ile
225                 230                 235                 240

Phe Leu Leu Glu His Pro Asn Pro Lys Gly Arg Tyr Asn Cys Ser Pro
                245                 250                 255

Phe Ile Val Pro Ile Glu Glu Ile Ala Glu Ile Ile Ser Ala Lys Tyr
            260                 265                 270

Pro Glu Tyr Gln Ile Pro Ala Leu Glu Glu Val Lys Glu Ile Lys Gly
        275                 280                 285

Ala Lys Leu Pro His Leu Thr Ser Gln Lys Leu Val Asp Ala Gly Phe
```

-continued

```
            290                 295                 300
Glu Phe Lys Tyr Ser Val Glu Asp Ile Phe Thr Asp Ala Ile Glu Cys
305                 310                 315                 320

Cys Lys Glu Lys Gly Tyr Leu
                325
```

(2) INFORMATION FOR SEQ ID NO:9:

(i) SEQUENCE CHARACTERISTICS:
        (A) LENGTH: 326 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:9:

```
Met Ala Glu Gly Lys Gly Arg Val Cys Val Thr Gly Thr Gly Phe
1                 5                  10                  15

Leu Gly Ser Trp Ile Ile Lys Ser Leu Leu Glu Asn Gly Tyr Ser Val
                20                  25                  30

Asn Thr Thr Ile Arg Ala Asp Pro Glu Arg Lys Arg Asp Val Ser Phe
                35                  40                  45

Leu Thr Asn Leu Pro Gly Ala Ser Glu Lys Leu His Phe Phe Asn Ala
50                  55                  60

Asp Leu Ser Asn Pro Asp Ser Phe Ala Ala Ile Glu Gly Cys Val
65                  70                  75                  80

Gly Ile Phe His Thr Ala Ser Pro Ile Asp Phe Ala Val Ser Glu Pro
                85                  90                  95

Glu Glu Ile Val Thr Lys Arg Thr Val Asp Gly Ala Leu Gly Ile Leu
                100                 105                 110

Lys Ala Cys Val Asn Ser Lys Thr Val Lys Arg Phe Ile Tyr Thr Ser
                115                 120                 125

Ser Gly Ser Ala Val Ser Phe Asn Gly Lys Asp Lys Asp Val Leu Asp
                130                 135                 140

Glu Ser Asp Trp Ser Asp Val Asp Leu Leu Arg Ser Val Lys Pro Phe
145                 150                 155                 160

Gly Trp Asn Tyr Ala Val Ser Lys Thr Leu Ala Glu Lys Ala Val Leu
                165                 170                 175

Glu Phe Gly Glu Gln Asn Gly Ile Asp Val Val Thr Leu Ile Leu Pro
                180                 185                 190

Phe Ile Val Gly Arg Phe Val Cys Pro Lys Leu Pro Asp Ser Ile Glu
                195                 200                 205

Lys Ala Leu Val Leu Val Leu Gly Lys Lys Glu Gln Ile Gly Val Thr
210                 215                 220

Arg Phe His Met Val His Val Asp Asp Val Ala Arg Ala His Ile Tyr
225                 230                 235                 240

Leu Leu Glu Asn Ser Val Pro Gly Gly Arg Tyr Asn Cys Ser Pro Phe
                245                 250                 255

Ile Val Pro Ile Glu Glu Met Ser Gln Leu Leu Ser Ala Lys Tyr Pro
                260                 265                 270

Glu Tyr Gln Ile Leu Thr Val Asp Glu Leu Lys Glu Ile Lys Gly Ala
                275                 280                 285

Arg Leu Pro Asp Leu Asn Thr Lys Lys Leu Val Asp Ala Gly Phe Asp
                290                 295                 300

Phe Lys Tyr Thr Ile Glu Asp Met Phe Asp Asp Ala Ile Gln Cys Cys
```

```
                305               310               315               320
Lys Glu Lys Gly Tyr Leu
                325
```